United States Patent
Horzewski et al.

(10) Patent No.: US 7,241,270 B2
(45) Date of Patent: Jul. 10, 2007

(54) SYSTEMS AND METHODS FOR MONITORING AND ENABLING USE OF A MEDICAL INSTRUMENT

(75) Inventors: Michael J Horzewski, San Jose, CA (US); Veijo T Suorsa, Sunnyvale, CA (US); Todd A Thompson, San Jose, CA (US)

(73) Assignee: Timi 3 Systems Inc., Santa Clara, CA (US)

( * ) Notice: Subject to any disclaimer, the term of this patent is extended or adjusted under 35 U.S.C. 154(b) by 946 days.

(21) Appl. No.: 10/202,447

(22) Filed: Jul. 24, 2002

(65) Prior Publication Data

US 2003/0055363 A1 Mar. 20, 2003

Related U.S. Application Data

(63) Continuation-in-part of application No. 09/935,908, filed on Aug. 23, 2001, which is a continuation-in-part of application No. 09/645,662, filed on Aug. 24, 2000, now abandoned.

(51) Int. Cl.
*A61N 7/00* (2006.01)
(52) U.S. Cl. .................................................. 601/2
(58) Field of Classification Search ................ 600/300, 600/407, 437, 439; 128/897, 898; 604/22; 601/2–4
See application file for complete search history.

(56) References Cited

U.S. PATENT DOCUMENTS

| | | |
|---|---|---|
| 3,985,337 A | 10/1976 | Gripe et al. |
| 4,563,261 A | 1/1986 | Staab et al. |
| 4,651,716 A | 3/1987 | Forester et al. |
| 4,740,287 A | 4/1988 | Cawlfield |
| 4,791,915 A | 12/1988 | Barsotti et al. |
| 4,955,365 A | 9/1990 | Fry et al. |

(Continued)

FOREIGN PATENT DOCUMENTS

JP 8089549 4/1996

(Continued)

OTHER PUBLICATIONS

Lindblad et al., "Effect of Vibration on a Canine Cutaneous Artery," Am J. Physiol. 250 H519-H523 (1986).

(Continued)

*Primary Examiner*—Ruth S. Smith
(74) *Attorney, Agent, or Firm*—Ryan, Kromholz, and Manion, S.C.

(57) ABSTRACT

Systems and methods monitor and enable the use of a medical instrument that is configured to be operated in a prescribed manner. The systems and methods employ a use register sized and configured to be carried by the medical instrument, which comprises a memory field for recording a start date and time at an instance of first operation of the medical instrument. The systems and methods also employ a use monitoring controller, which is adapted and configured to be coupled to the use register. The use monitoring controller includes a start validation function that compares the start date and time to a present real date and time and provides a start validation output based upon the comparison. The use monitoring controller also includes an enablement function that enables operation of the medical instrument only if the start validation output meets prescribed criteria.

4 Claims, 8 Drawing Sheets

U.S. PATENT DOCUMENTS

| | | | |
|---|---|---|---|
| 4,966,131 A | 10/1990 | Houghton et al. | |
| 5,024,829 A | 6/1991 | Berger et al. | |
| 5,159,838 A | 11/1992 | Lynnworth | |
| 5,190,766 A | 3/1993 | Ishihara | |
| 5,230,334 A | 7/1993 | Klopotek et al. | |
| 5,267,223 A | 11/1993 | Flanagan et al. | |
| 5,291,894 A | 3/1994 | Nagy | |
| 5,313,935 A * | 5/1994 | Kortenbach et al. | 600/117 |
| 5,359,993 A * | 11/1994 | Slater et al. | 600/133 |
| 5,394,047 A | 2/1995 | Scharlack et al. | |
| 5,400,267 A * | 3/1995 | Denen et al. | 702/59 |
| 5,413,550 A | 5/1995 | Castel | |
| 5,454,373 A | 10/1995 | Koger et al. | |
| 5,520,612 A | 5/1996 | Winder et al. | |
| 5,531,119 A | 7/1996 | Meyers | |
| 5,556,372 A | 9/1996 | Talish et al. | |
| 5,580,575 A | 12/1996 | Unger et al. | |
| 5,626,554 A | 5/1997 | Ryaby et al. | |
| 5,695,460 A | 12/1997 | Siegel et al. | |
| 5,698,531 A | 12/1997 | Nabel et al. | |
| 5,720,304 A | 2/1998 | Omura | |
| 5,725,482 A | 3/1998 | Bishop | |
| 5,762,616 A | 6/1998 | Talish | |
| 5,879,314 A | 3/1999 | Peterson et al. | |
| 5,913,834 A | 6/1999 | Francais | |
| 5,991,355 A * | 11/1999 | Dahlke | 377/15 |
| 6,080,187 A | 6/2000 | Alt et al. | |
| 6,095,979 A | 8/2000 | Ohtomo | |
| 6,126,619 A | 10/2000 | Peterson et al. | |
| 6,200,259 B1 | 3/2001 | March | |
| 6,237,604 B1 * | 5/2001 | Burnside et al. | 128/897 |
| 6,254,573 B1 | 7/2001 | Haim et al. | |
| 6,261,537 B1 | 7/2001 | Klaveness et al. | |
| 6,273,864 B1 | 8/2001 | Duarte et al. | |
| 6,295,330 B1 * | 9/2001 | Skog et al. | 377/15 |
| 6,398,772 B1 | 6/2002 | Bond et al. | |
| 6,432,070 B1 | 8/2002 | Talish et al. | |
| 6,434,539 B1 | 8/2002 | Woodsum et al. | |
| 6,477,426 B1 | 11/2002 | Fenn et al. | |
| 6,511,429 B1 | 1/2003 | Fatemi et al. | |
| 6,577,042 B2 | 6/2003 | Lee et al. | |
| 6,635,017 B1 | 10/2003 | Moehring et al. | |
| 6,682,502 B2 | 1/2004 | Bond et al. | |
| 6,979,812 B2 * | 12/2005 | Al-Ali | 250/214.1 |
| 7,048,687 B1 * | 5/2006 | Reuss et al. | 600/300 |
| 2002/0082528 A1 | 6/2002 | Friedman et al. | |
| 2003/0157025 A1 | 8/2003 | Unger et al. | |
| 2003/0204141 A1 | 10/2003 | Nock et al. | |
| 2004/0133066 A1 | 7/2004 | Mann et al. | |
| 2004/0230252 A1 | 11/2004 | Kullok et al. | |
| 2005/0004460 A1 | 1/2005 | Taylor et al. | |

FOREIGN PATENT DOCUMENTS

WO     WO 85/03634     8/1985

OTHER PUBLICATIONS

Ljung et al., "Inhibition of Vascular Smooth Muscle Contraction by Vibrations" Abstract Acta Physiol. Scand., 396, Suppl., p. 95 (1973).

Ng, K. et al., "Therapeutic Ultrasound: Its Application in Drug Delivery"; Medicinal Re-search Reviews, vol. 22, No. 2, 204-223, 2002.

Tachibana, K. et al., "The Use of Ultrasound for Drug Delivery"; Echocardiography, vol. 18, May 2001.

Hull, W. et al., "Heat-Enhanced Transdermal Drug Delivery: A Survey Paper"; The Journal of Applied Research, vol. 2, No. 1, Winter 2002.

Cho, C.W., et al, "Ultrasound induced mild hyperthermia as a novel approach to increase drug intake in brain microvessel endothelial cells", Pharm Res. Aug. 2002;19(8);1123-9.

Koiwa et al., "The effect of diastolic vibration on the coronary flow rate in the canine heart with ischemia" Journal Cardiovasc Diagn Procedures, 12; p. 110 (1994).

Zagzebski, "Essentials of Ultrasound Physics," Physics of Diagnostic Ultrasound, p. 5 (1996).

Google Website: "Hearing Pitch or Sound Frequencies—Succeed Through Using Your Senses"—"Hearing Pitch or Sound Frequencies" by Ron Kurtus (Mar. 7, 2001).

* cited by examiner

US 7,241,270 B2

SYSTEMS AND METHODS FOR MONITORING AND ENABLING USE OF A MEDICAL INSTRUMENT

RELATED APPLICATION

This application is a continuation-in-part of co-pending U.S. Pat. application Ser. No. 09/935,908, filed Aug. 23, 2001, which is a continuation -in-part of U.S. patent application Ser. No. 09/645,662, filed Aug. 24, 2000, and entitled "Systems and Methods for Enhancing Blood Perfusion Using Ultrasound Energy" (Abandoned), which are both incorporated herein by reference.

FIELD OF THE INVENTION

This invention relates to systems and methods for increasing blood perfusion, e.g., in the treatment of myocardial infarction, strokes, and vascular diseases.

BACKGROUND OF THE INVENTION

High frequency (5 MHz to 7 MHz) ultrasound has been widely used for diagnostic purposes. Potential therapeutic uses for ultrasound have also been more recently suggested. For example, it has been suggested that high power, lower frequency ultrasound can be focused upon a blood clot to cause it to break apart and dissolve. The interaction between lower frequency ultrasound in the presence of a thrombolytic agent has also been observed to assist in the breakdown or dissolution of thrombi. The effects of ultrasound upon enhanced blood perfusion have also been observed.

While the therapeutic potential of these uses for ultrasound has been recognized, their clinical promise has yet to be fully realized. Treatment modalities that can apply ultrasound in a therapeutic way are designed with the premise that they will be operated by trained medical personnel in a conventional fixed-site medical setting. They assume the presence of trained medical personnel in a non-mobile environment, where electrical service is always available. Still, people typically experience the effects of impaired blood perfusion suddenly in public and private settings. These people in need must be transported from the public or private settings to the fixed-site medical facility before ultrasonic treatment modalities can begin. Treatment time (which is often critical in the early stages of impaired blood perfusion) is lost as transportation occurs. Even within the fixed-site medical facility, people undergoing treatment need to be moved from one care unit to another. Ultrasonic treatment modalities must be suspended while the person is moved.

SUMMARY OF THE INVENTION

The invention provides systems and methods that monitor and enable the use of a medical instrument that is configured to be operated in a prescribed manner.

According to one aspect of the invention, the systems and methods employ a use register sized and configured to be carried by the medical instrument, which comprises a memory field for recording a start date and time at an instance of first operation of the medical instrument. The systems and methods also employ a use monitoring controller, which is adapted and configured to be coupled to the use register. The use monitoring controller includes a start validation function that compares the start date and time to a present real date and time and provides a start validation output based upon the comparison. The use monitoring controller also includes an enablement function that enables operation of the medical instrument only if the start validation output meets prescribed criteria.

According to another aspect of the invention, the systems and methods comprise a use register that is sized and configured to be carried by the medical instrument. The use register comprises a memory field for recording a prescribed copyright notice. The systems and methods also include a use monitoring controller that is adapted and configured to be coupled to the use register. The use monitoring controller includes a copyright validation function that assesses the contents of the memory field and provides a copyright validation output based upon the assessment. The use monitoring controller also includes an enablement function that enables operation of the medical instrument only if the copyright validation output meets prescribed criteria.

In one embodiment, the medical instrument comprises an ultrasound energy applicator that includes an ultrasound transducer adapted and configured to be coupled to an ultrasound generator for operation. In this embodiment, the use register is sized and configured to be carried by the ultrasound applicator.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with the therapeutic indication of providing increased blood perfusion by the transcutaneous application of ultrasonic energy. That is because the features and advantages of the invention are well suited to this therapeutic indication. Still, it should be appreciated that many aspects of the invention can be applied to achieve other diagnostic or therapeutic objectives as well.

Furthermore, in describing the various aspects of the invention in the context of the illustrated embodiment, the region targeted for an increase in blood perfusion is the thoracic cavity (i.e., the space where the heart and lungs are contained). It should be appreciated, however, that the features of invention have application in other regions of the body, too, for example, in the arms, legs, or brain.

I. System for Providing Noninvasive Ultrasound-Assisted Blood Perfusion

Figure 1:
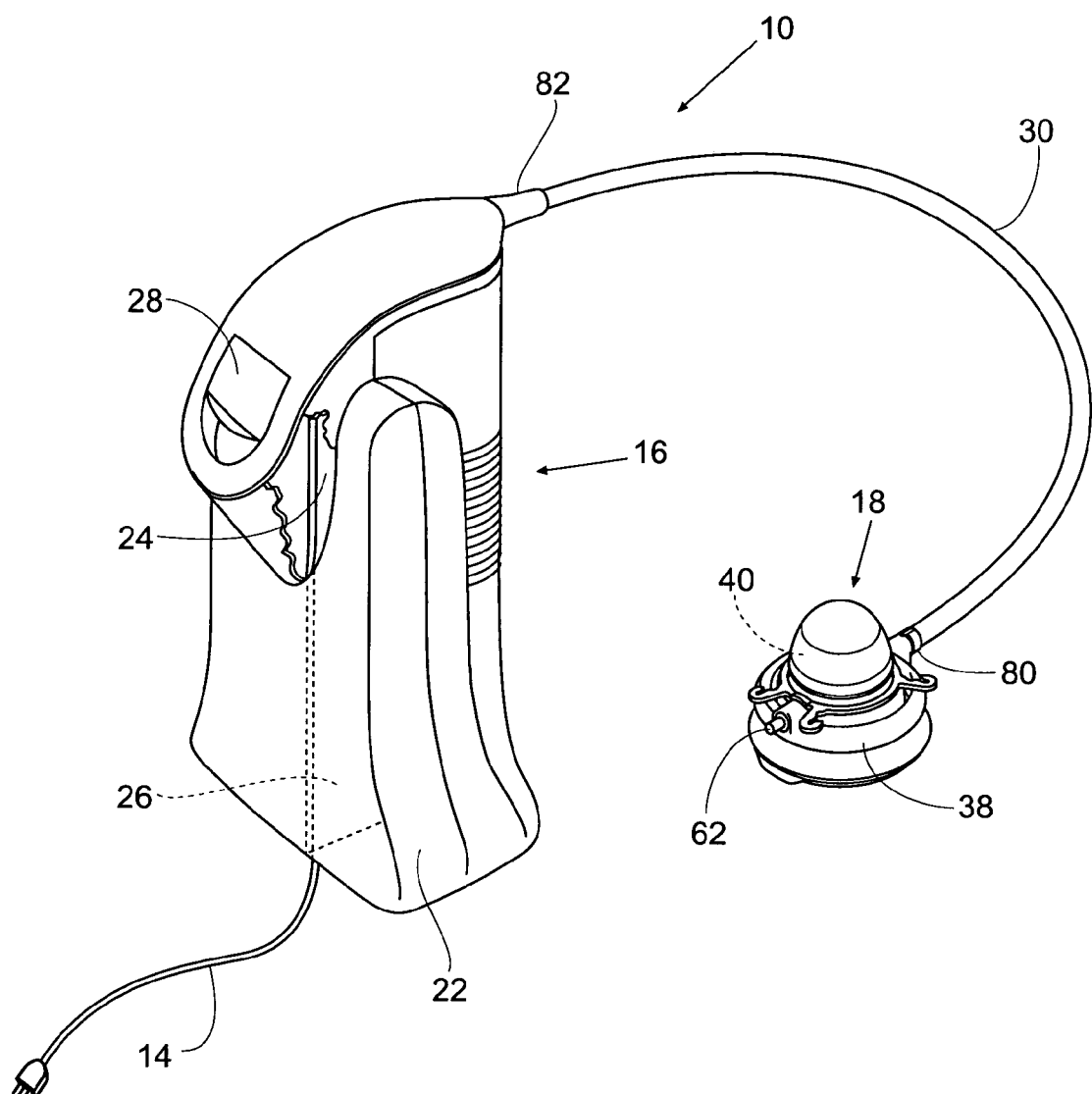
FIG. 1 is a perspective view of a system for transcutaneously applying ultrasound energy to affect increased blood perfusion.

FIG. 1 schematically shows a compact, portable therapeutic system 10 that makes it possible to treat a person who needs or who is likely to need an increase in the flow rate or perfusion of circulating blood.

The system 10 includes durable and disposable equipment and materials necessary to treat the person at a designated treatment location. In use, the system 10 affects increased blood perfusion by transcutaneously applying ultrasonic energy.

Figure 5:
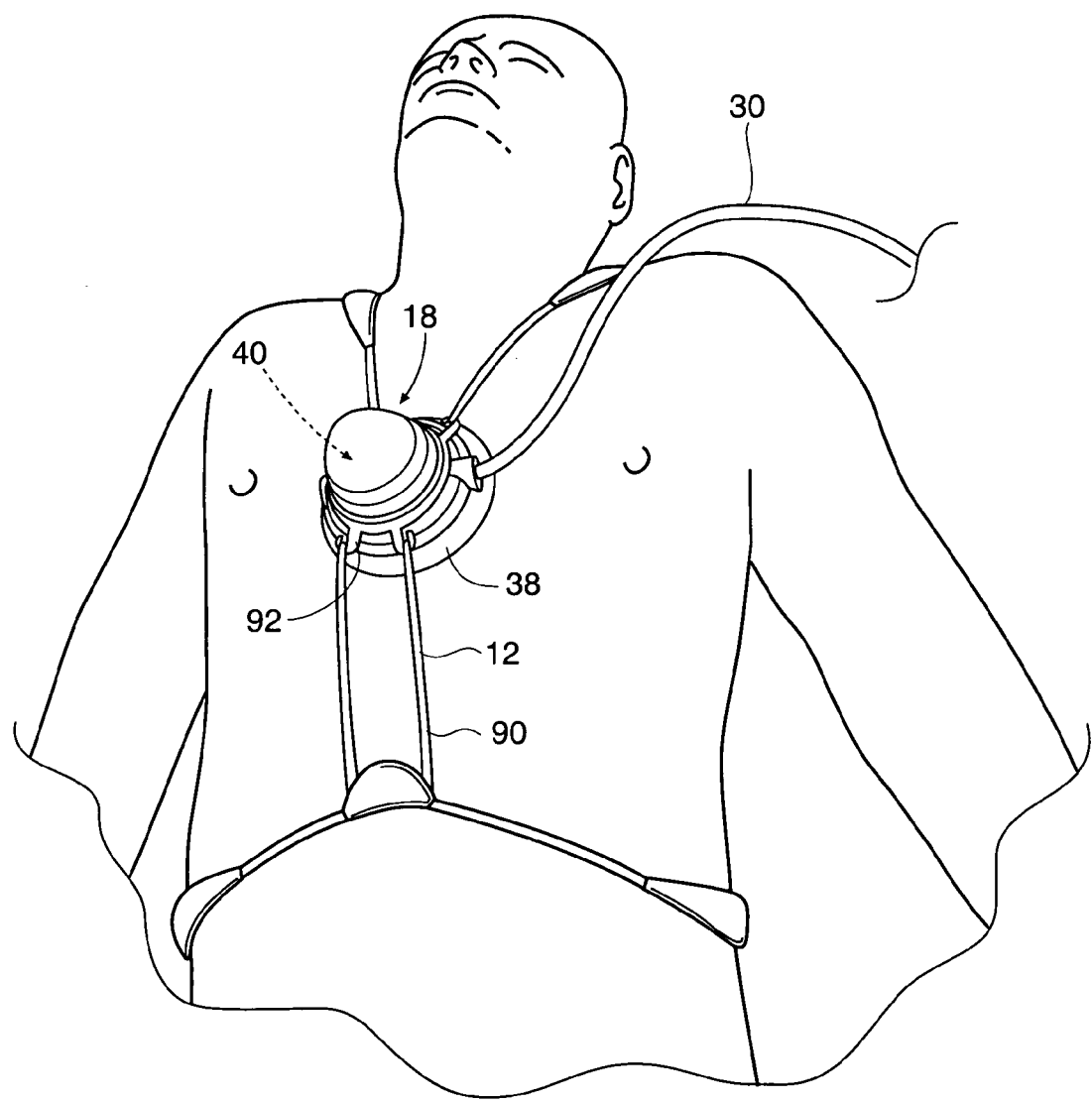
FIG. 5 is a view of the applicator shown in FIG. 2 held by a stabilization assembly in a secure position overlaying the sternum of a patient, to transcutaneously direct ultrasonic energy, e.g., toward the vasculature of the heart.

As FIG. 1 shows, the system 10 includes at the treatment location an ultrasound generating machine 16. The system 10 also includes at the treatment location at least one ultrasound applicator 18, which is coupled to the machine 16 during use. As FIG. 5 shows, the system 10 also includes an assembly 12 for use with the applicator 18 to stabilize the position of the applicator 18 on a patient for hands-free use. In the illustrated embodiment (see FIG. 5), the applicator 18 is secured against movement on a person's thorax, overlaying the sternum, to direct ultrasonic energy toward the vasculature of the heart.

The location where treatment occurs can vary. It can be a traditional clinical setting, where support and assistance by one or more medically trained care givers are immediately available to the person, such as inside a hospital, e.g., in an emergency room, catheter lab, operating room, or critical care unit. However, due to the purposeful design of the system 10, the location need not be confined to a traditional clinical setting. The location can comprise a mobile setting, such as an ambulance, helicopter, airplane, or like vehicle used to convey the person to a hospital or another clinical treatment center. The location can even comprise an everyday, public setting, such as on a cruise ship, or at a sports stadium or airport, or a private setting, such as in a person's home, where the effects of low blood perfusion can arise.

By purposeful design of durable and disposable equipment, the system 10 can make it possible to initiate treatment of a reduced blood perfusion incident in a non-clinical, even mobile location, outside a traditional medical setting. The system thereby makes effective use of the critical time period before the person enters a hospital or another traditional medical treatment center.

The features and operation of the system 10 will now be described in greater detail.

A. The Ultrasound Generator

FIG. 1 shows a representative embodiment of the ultrasound generating machine 16. The machine 16 can also be called an "ultrasound generator." The machine 16 is intended to be a durable item capable of long term, maintenance free use.

As shown in FIG. 1, the machine 16 can be variously sized and shaped to present a lightweight and portable unit, presenting a compact footprint suited for transport. The machine 16 can be sized and shaped to be mounted at bedside, or to be placed on a table top or otherwise occupy a relatively small surface area. This allows the machine 16 to travel with the patient within an ambulance, airplane, helicopter, or other transport vehicle where space is at a premium. This also makes possible the placement of the machine 16 in a non-obtrusive way within a private home setting, such as for the treatment of chronic angina.

In the illustrated embodiment, the machine 16 includes a chassis 22, which, for example, can be made of molded plastic or metal or both. The chassis 22 houses a module 24 for generating electric signals. The signals are conveyed to the applicator 18 by an interconnect 30 to be transformed into ultrasonic energy. A controller 26, also housed within the chassis 22 (but which could be external of the chassis 22, if desired), is coupled to the module 24 to govern the operation of the module 24. Further desirable technical features of the controller 26 will be described later.

The machine 16 also preferably includes an operator interface 28. Using the interface 28, the operator inputs information to the controller 26 to affect the operating mode of the module 24. Through the interface 28, the controller 26 also outputs status information for viewing by the operator. The interface 28 can provide a visual readout, printer output, or an electronic copy of selected information regarding the treatment. The interface 28 is shown as being carried on the chassis 22, but it could be located external of the chassis 22 as well.

The machine 16 includes a power cord 14 for coupling to a conventional electrical outlet, to provide operating power to the machine 16. The machine 16 can also include a battery module (not shown) housed within the chassis 22, which enables use of the machine 16 in the absence or interruption of electrical service. The battery module can comprise rechargeable batteries, that can be built in the chassis 22 or, alternatively, be removed from the chassis 22 for recharge. Likewise, the battery module (or the machine 16 itself) can include a built-in or removable battery recharger. Alternatively, the battery module can comprise disposable batteries, which can be removed for replacement.

Power for the machine 16 can also be supplied by an external battery and/or line power module outside the chassis 22. The battery and/or line power module is releasably coupled at time of use to the components within the chassis 22, e.g., via a power distribution module within the chassis 22.

The provision of battery power for the machine 16 frees the machine 16 from the confines surrounding use of conventional ultrasound equipment, caused by their dependency upon electrical service. This feature makes it possible for the machine 16 to provide a treatment modality that continuously "follows the patient," as the patient is being transported inside a patient transport vehicle, or as the patient is being shuttled between different locations within a treatment facility, e.g., from the emergency room to a holding area within or outside the emergency room.

In a representative embodiment, the chassis 22 measures about 12 inches×about 8 inches×about 8 inches and weighs about 9 pounds.

B. The Ultrasound Applicator

As shown in FIG. 5, the applicator 18 can also be called the "patient interface." The applicator 18 comprises the link between the machine 16 and the treatment site within the thoracic cavity of the person undergoing treatment. The applicator 18 converts electrical signals from the machine 16 to ultrasonic energy, and further directs the ultrasonic energy to the targeted treatment site.

Desirably, the applicator 18 is intended to be a disposable item. At least one applicator 18 is coupled to the machine 16 via the interconnect 30 at the beginning a treatment session. The applicator 18 is preferably decoupled from the interconnect 30 (as FIG. 1 shows) and discarded upon the completing the treatment session. However, if desired, the applicator 18 can be designed to accommodate more than a single use.

Figure 2:
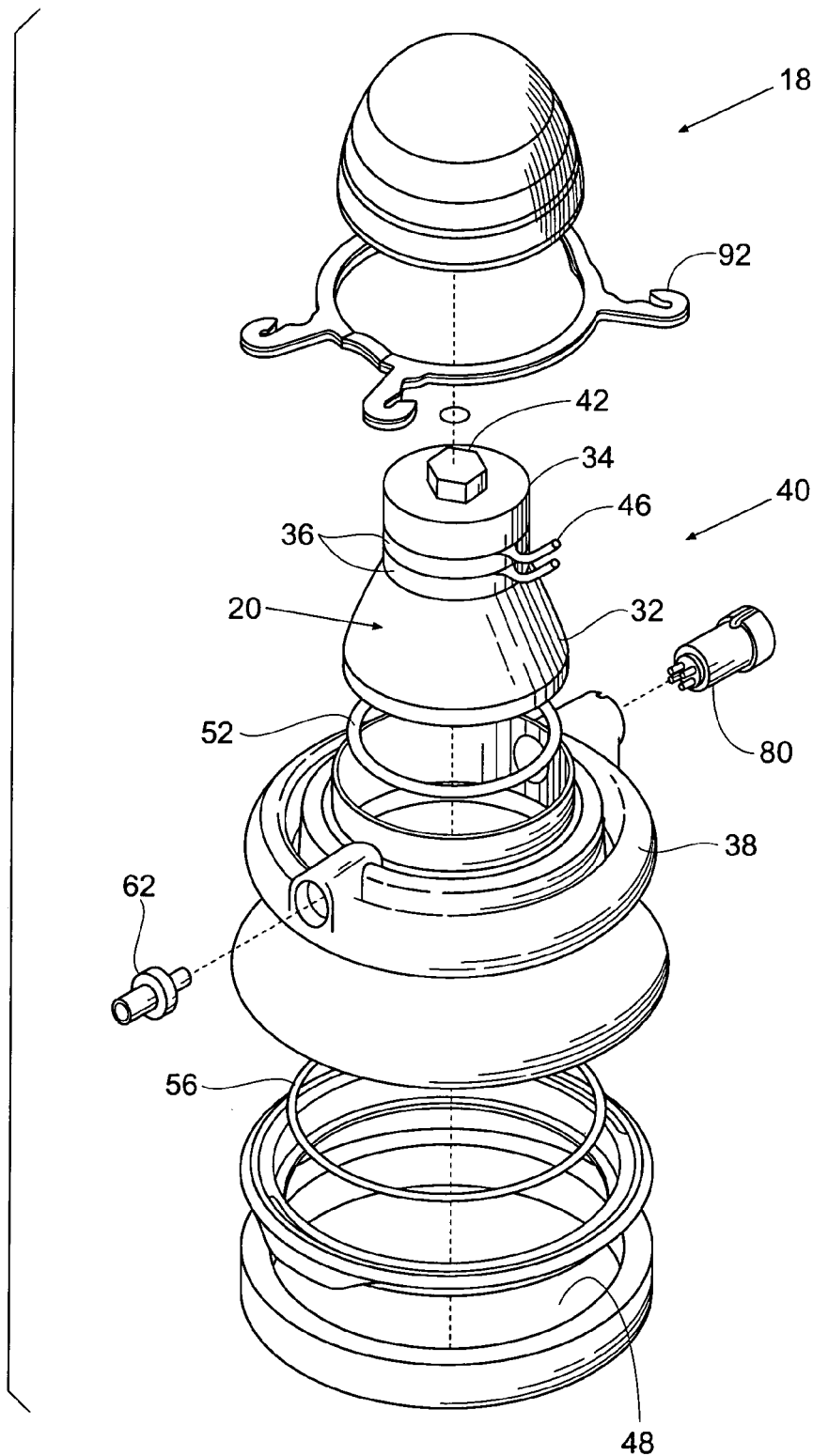
FIG. 2 is an enlarged exploded perspective view of an ultrasound applicator that forms a part of the system shown in FIG. 1.
Figure 3:
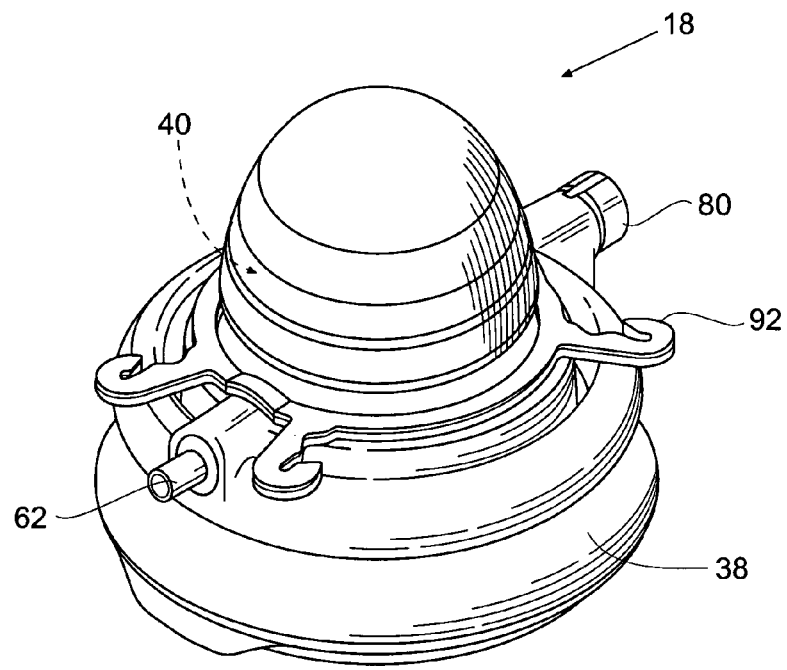
FIG. 3 is an enlarged assembled perspective view of the ultrasound applicator shown in FIG. 2.

As FIGS. 2 and 3 show, the ultrasound applicator 18 includes a shaped metal or plastic body 38 ergonomically sized to be comfortably grasped and manipulated in one hand. The body 38 houses and supports at least one ultrasound transducer 40 (see FIG. 3).

In the illustrated embodiment, the ultrasound transducer 40 comprises an acoustic stack 20. The acoustic stack 20 comprises a front mass piece 32, a back mass piece 34, and one or more piezoelctric elements 36, which are bolted together. The back mass piece 34 comprises an annular ring of material having relatively high acoustic impedance, e.g., steel or stainless steel: "Acoustic impedance" is defined as the product of the density of the material and the speed of sound.

The front mass piece 32 comprises a cone-shaped piece of material having relatively low acoustic impedance, e.g., aluminum or magnesium. The piezoelectric elements 36 are annular rings made of piezoelectric material, e.g., PZT. An internally threaded hole or the like receives a bolt 42 that mechanically biases the acoustic stack 20. A bolt 42 that can be used for this purpose is shown in U.S. Pat. No. 2,930,912. The bolt 42 can extend entirely through the front mass piece 32 or, the bolt 42 can extend through only a portion of the front mass piece 32 (see FIG. 7).

Figure 6:
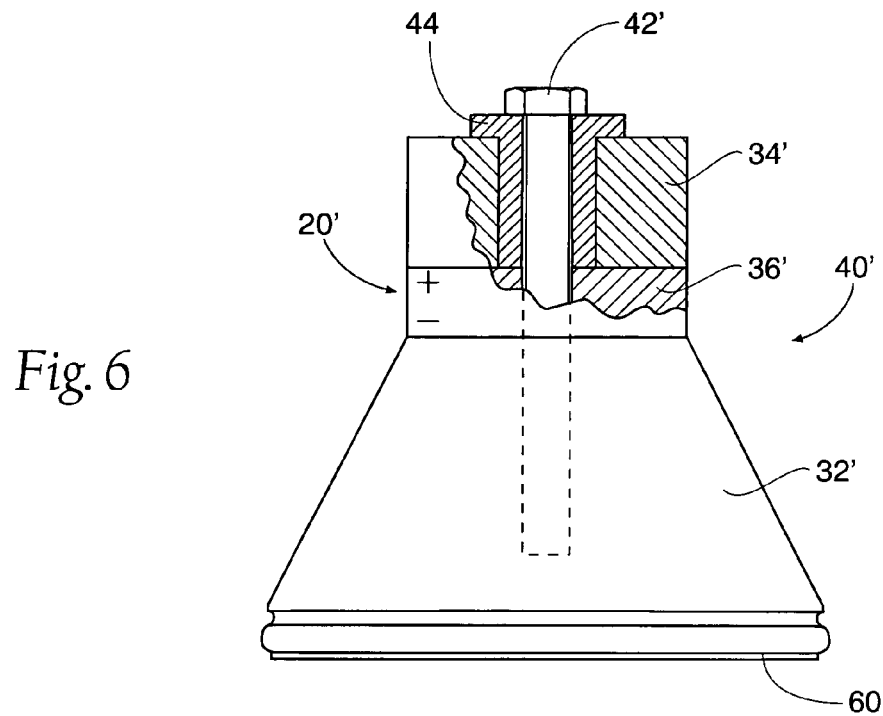
FIG. 6 is a side elevation view, with portions broken away and in section, of an acoustic stack that can be incorporated into the applicator shown in FIG. 2.

In an alternative embodiment (see FIG. 6), the acoustic stack 20' of a transducer 40' can comprise a single piezoelectric element 36' sandwiched between front and back mass pieces 32' and 34'. In this arrangement, the back mass piece 34' is electrically insulated from the front mass piece 32' by, e.g., an insulating sleeve and washer 44.

The piezoelectric element(s) 36/36' have electrodes 46 (see FIG. 2) on major positive and negative flat surfaces. The electrodes 46 electrically connect the accoustic stack 20 of the transducer 40 to the electrical signal generating module 24 of the machine 16. When electrical energy at an appropriate frequency is applied to the electrodes 46, the piezoelectric elements 36/36' convert the electrical energy into mechanical (i.e., ultrasonic) energy in the form of mechanical vibration.

The mechanical vibration created by the transducer 40/40' is coupled to a patient through a transducer bladder 48, which rests on a skin surface. The bladder 48 defines a bladder chamber 50 (see FIG. 4) between it and the front mass piece 32. The bladder chamber 50 spaces the front mass piece 32 a set distance from the patient's skin. The bladder chamber 50 accommodates a volume of an acoustic coupling media liquid, e.g., liquid, gel, oil, or polymer, that is conductive to ultrasonic energy, to further cushion the contact between the applicator 18 and the skin. The presence of the acoustic coupling media also makes the acoustic contact area of the bladder 48 more conforming to the local skin topography.

Desirably, an acoustic coupling medium is also applied between the bladder 48 and the skin surface. The coupling medium can comprise, e.g., a gel material (such as AQUASONIC® 100, by Parker Laboratories, Inc., Fairfield, N.J.). The external material can possess sticky or tacky properties, to further enhance the securement of the applicator 18 to the skin.

In the illustrated embodiment, the bladder 48 and bladder chamber 50 together form an integrated part of the applicator 18. Alternatively, the bladder 48 and bladder chamber 50 can be formed by a separate molded component, e.g., a gel or liquid filled pad, which is supplied separately. A molded gel filled pad adaptable to this purpose is the AQUAFLEX® Ultrasound Gel Pad sold by Parker Laboratories (Fairfield, N.J.).

In a representative embodiment, the front mass piece 32 of the acoustic stack 20 measures about 2 inches in diameter, whereas the acoustic contact area formed by the bladder 48 measures about 4 inches in diameter. An applicator 18 that presents an acoustic contact area of larger diameter than the front mass piece 32 of the transducer 40 makes possible an ergonomic geometry that enables single-handed manipulation during set-up, even in confined quarters, and further provides(with the assembly 12) hands-free stability during use. In a representative embodiment, the applicator 18 measures about 4 inches in diameter about the bladder 48, about 4 inches in height, and weighs about one pound.

An O-ring 52 (see FIG. 4) is captured within a groove 54 in the body 38 of the applicator 18 and a groove 84 on the front mass piece 32 of the transducer 40. The o-ring 52 seals the bladder chamber 50 and prevents liquid in the chamber 50 from contacting the sides of the front mass piece 32. Thus, as FIG. 4 shows, only the outer surface of the front mass piece 32 is in contact with the acoustic coupling medium within the chamber 50.

Desirably, the material of the O-ring 52 is selected to possess elasticity sufficient to allow the acoustic stack 20 of the transducer 40 to vibrate freely in a piston-like fashion within the transducer body 38. Still, the material of the O-ring 52 is selected to be sturdy enough to prevent the acoustic stack 20, while vibrating, from popping out of the grooves 54 and 84.

In a representative embodiment, the O-ring 52 is formed from nitrile rubber (Buna-N) having a hardness of about 30 Shore A to about 100 Shore A. Preferably, the O-ring 52 has a hardness of about 65 Shore A to about 75 Shore A.

Figure 4:
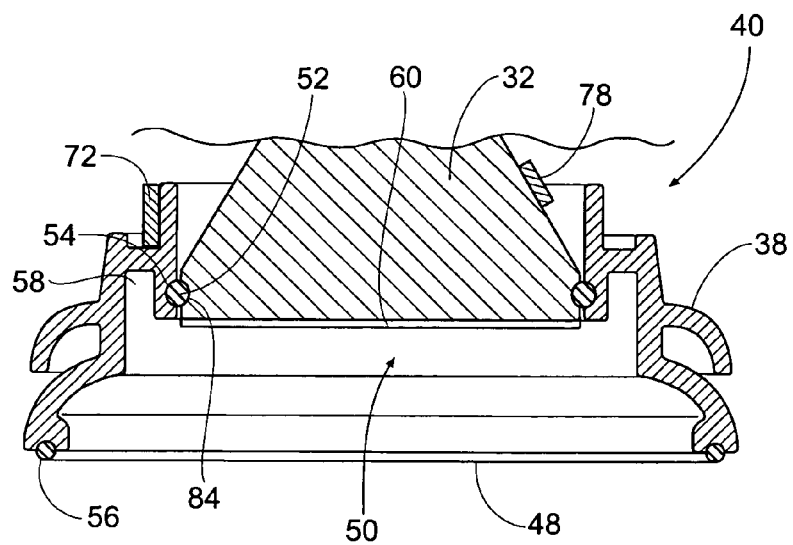
FIG. 4 is a side section view of the acoustic contact area of the ultrasound applicator shown in FIG. 2.

The bladder 48 is stretched across the face of the bladder chamber 50 and is preferably also locked in place with another O-ring 56 (see FIG. 4). A membrane ring may also be used to prevent the O-ring 56 from popping loose. The membrane ring desirably has a layer or layers of soft material (e.g., foam) for contacting the skin.

Localized skin surface heating effects may arise by the presence of air bubbles trapped between the acoustic contact area (i.e., the surface of the bladder 48) and the individual's skin. In the presence of ultrasonic energy, the air bubbles vibrate, and thereby may cause cavitation and attendant conductive heating effects at the skin surface. To minimize the collection of air bubbles along the acoustic contact area, the bladder 48 desirably presents a flexible, essentially flat radiating surface contour where it contacts the individual's skin (see FIG. 4), or a flexible, outwardly bowed or convex radiating surface contour(i.e., curved away from the front mass piece) where it contacts with or conducts acoustic energy to the individual's skin. Either a flexible flat or convex surface contour can "mold" evenly to the individual's skin topography, to thereby mediate against the collection and concentration of air bubbles in the contact area where skin contact occurs.

To further mediate against cavitation-caused localized skin surface heating, the interior of the bladder chamber 50 can include a recessed well region 58 surrounding the front mass piece 32. The well region 58 is located at a higher gravity position than the plane of the front mass piece 32. Air bubbles that may form in fluid located in the bladder chamber 50 collect in the well region 58 away from the ultrasonic energy beam path.

Figure 7:
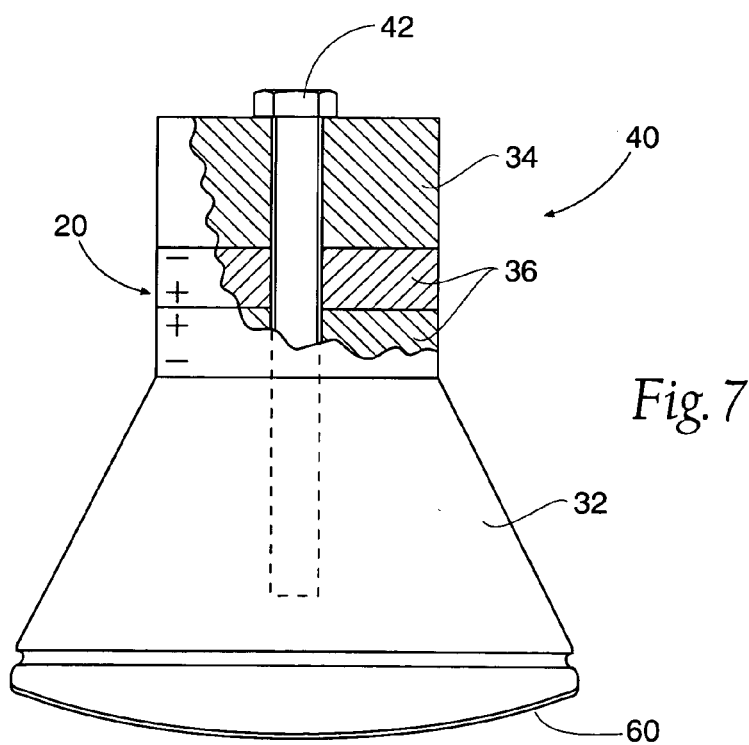
FIG. 7 is a side elevation view, with portions broken away and in section, of an acoustic stack that can be incorporated into the applicator shown in FIG. 2.

The front mass piece 32 desirably possesses either a flat radiating surface (as FIG. 4 shows) or a convex radiating surface (as FIG. 7 shows). The convex radiation surface directs air bubbles off the radiating surface. The radiating surface of the front mass piece may also be coated with a hydrophilic material 60 (see FIG. 4) to prevent air bubbles from sticking.

The transducer 40 may also include a reflux valve/liquid inlet port 62.

The interconnect 30 carries a distal connector 80 (see FIG. 2), designed to easily plug into a mating outlet in the applicator 18. A proximal connector 82 on the interconnect 30 likewise easily plugs into a mating outlet on the chassis 22 (see FIG. 1), which is itself coupled to the controller 26. In this way, the applicator 18 can be quickly connected to the machine 16 at time of use, and likewise quickly disconnected for discard once the treatment session is over. Other quick-connect coupling mechanisms can be used. It should also be appreciated that the interconnect 30 can be hard wired as an integrated component to the applicator 18 with a proximal quick-connector to plug into the chassis 22, or, vice versa, the interconnect 30 can be hard wired as an integrated component to the chassis 22 with a distal quick-connector to plug into the applicator 18.

As FIG. 5 shows, the stabilization assembly 12 allows the operator to temporarily but securely mount the applicator 18 against an exterior skin surface for use. In the illustrated embodiment, since the treatment site exists in the thoracic cavity, the attachment assembly 54 is fashioned to secure the applicator 18 on the person's thorax, overlaying the sternum or breastbone, as FIG. 5 shows.

The assembly 12 can be variously constructed. As shown in FIG. 5, the assembly 12 comprises straps 90 that pass through brackets 92 carried by the applicator 18. The straps 90 encircle the patient's neck and abdomen.

Just as the applicator 18 can be quickly coupled to the machine 16 at time of use, the stabilization assembly 12 also preferably makes the task of securing and removing the applicator 18 on the patient simple and intuitive. Thus, the stabilization assembly 12 makes it possible to secure the applicator 18 quickly and accurately in position on the patient in cramped quarters or while the person (and the system 10 itself) is in transit.

Desirably, when used to apply ultrasonic energy transcutaneously in the thoracic cavity to the heart, the front mass piece 32 is sized to deliver ultrasonic energy in a desired range of fundamental frequencies to substantially the entire targeted region (e.g., the heart). Generally speaking, the fundamental frequencies of ultrasound energy suited for transcutaneous delivery to the heart in the thoracic cavity to increase blood perfusion can lay in the range of about 500 kHz or less. Desirably, the fundamental frequencies for this indication lay in a frequency range of about 20 kHz to about 100 kHz, e.g., about 27 kHz.

II. Controlling the Application of Ultrasound Energy

To achieve the optimal application of ultrasound energy and the optimal therapeutic effect, the application of ultrasound energy should desirably incorporate one or more of the following features: (1) choice, or tuning, of the output frequency, (2) power ramping, (3) output power control, and (4) pulsed power.

A. Tuning of Output Frequency

Depending upon the treatment parameters and outcome desired, the controller 26 can operate a given transducer 40 at a fundamental frequency below about 50 kHz, or in a fundamental frequency range between about 50 kHz and about 1 MHz, or at fundamental frequencies above 1 MHz.

A given transducer 40 can be operated in either a pulsed or a continuous mode, or in a hybrid mode where both pulsed and continuous operation occurs in a determined or random sequence at one or more fundamental frequencies.

The applicator 18 can include multiple transducers 40 (or multiple applicators 18 can be employed simultaneously for the same effect), which can be individually conditioned by the controller 26 for operation in either pulsed or continuous mode, or both. For example, the multiple transducers 40 can all be conditioned by the controller 26 for pulsed mode operation, either individually or in overlapping synchrony. Alternatively, the multiple transducers 40 can all be conditioned by the controller 26 for continuous mode operation, either individually or in overlapping synchrony. Still alternatively, the multiple transducers 40 can be conditioned by the controller 26 for both pulsed and continuous mode operation, either individually or in overlapping synchrony.

One or more transducers 40 within an array of transducers 40 can also be operated at different fundamental frequencies. For example, one or more transducers 40 can be operated at about 25 kHz, while another one or more transducers 40 can be operated at about 100 kHz. More than two different fundamental frequencies can be used, e.g., about 25 kHz, about 50 kHz, and about 100 kHz.

Operation at different fundamental frequencies provides different effects. For example, given the same power level, at about 25 kHz, more cavitation effects are observed to dominate, while above 500 kHz, more heating effects are observed to dominate.

The controller 26 can trigger the fundamental frequency output according to time or a physiological event (such as ECG or respiration).

A given transducer 40 can be operated at a frequency within a certain range of frequencies suitable to the transducer 40. The optimal frequency for a given treatment is dependent on a number of factors, e.g., the magnitude of the fill volume of the bladder chamber 50; the characteristics of the acoustic coupling between the acoustic contact area (i.e., bladder 48) and the patient's skin; the morphology of the patient (e.g., size, weight, girth) which affect the transmission of ultrasound energy through the skin and within the body; the acoustic load impedance seen by the transducer 40.

Figure 9:
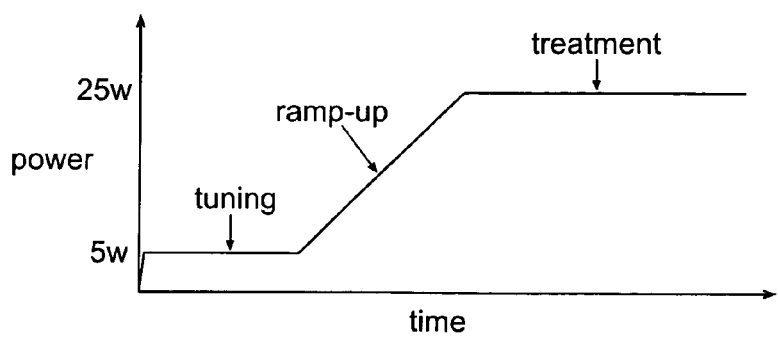
FIG. 9 graphically depicts the technical features of a power ramping function that the system shown in FIG. 1 can incorporate.
Figure 10:
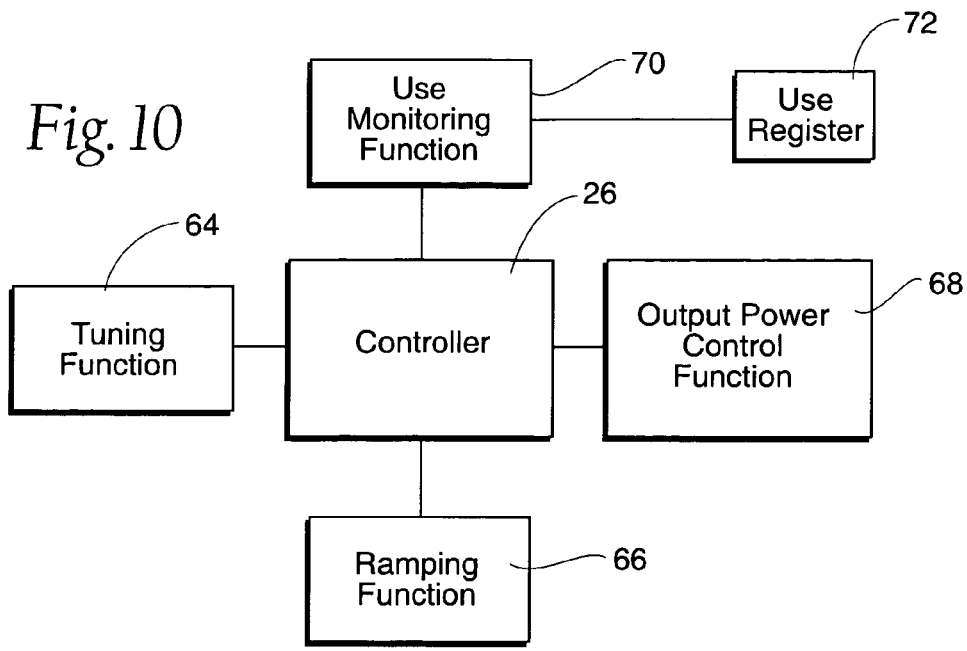
FIG. 10 is a schematic view of a controller that the system shown in FIG. 1 can incorporate, which includes a frequency tuning function, a power ramping function, an output power control function, and a use monitoring function.

As FIG. 10 shows, the controller 26 desirably includes a tuning function 64. The tuning function 64 selects an optimal frequency at the outset of each treatment session, taking into account at least some of the above-listed factors. In the illustrated embodiment (see FIGS. 8A to 8C), the tuning function sweeps the output frequency within a predetermined range of frequencies (f-start to f-stop). The frequency sweep can be and desirably is done at an output power level that is lower than the output power level of treatment (see FIG. 9). The frequency sweep can also be done in either a pulsed or a continuous mode, or in a hybrid mode. An optimal frequency of operation is selected based upon one or more parameters sensed during the sweeping operation.

Figure 8A:
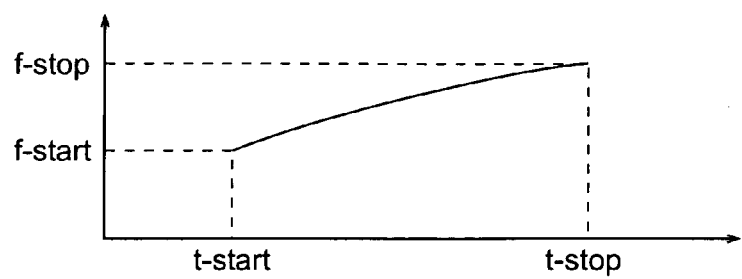
FIG. 8a to 8c graphically depict the technical features of a frequency tuning function that the system shown in FIG. 1 can incorporate.
Figure 8B:
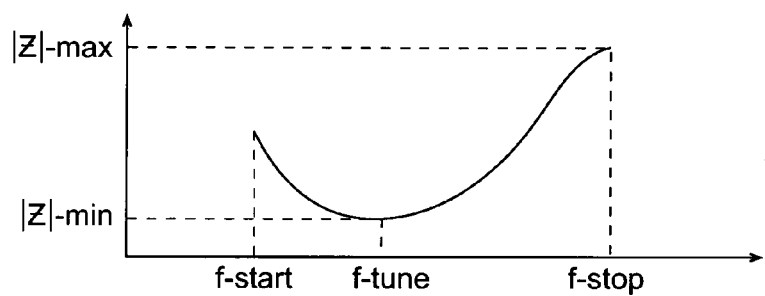
Figure 8C:
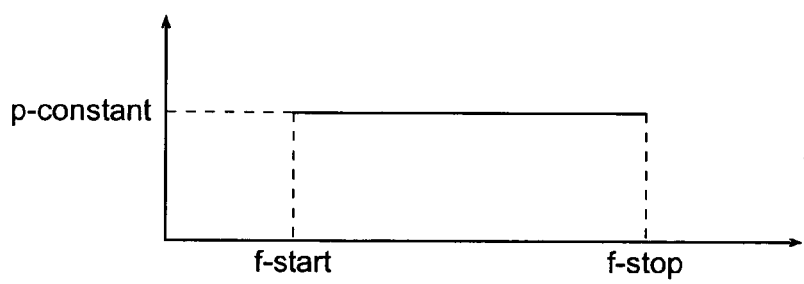

As FIG. 8A shows, the frequency sweep can progress from a lower frequency (f-start) to a higher frequency (f-stop), or vice versa. The sweep can proceed on a linear basis (as FIG. 8A also shows), or it can proceed on a non-linear basis, e.g., logarithmically or exponentially or based upon another mathematical function. The range of the actual frequency sweep may be different from the range that is used to determine the frequency of operation. For instance, the frequency span used for the determination of the frequency of operation may be smaller than the range of the actual sweep range.

In one frequency selection approach (see FIGS. 8A and 8C), while sweeping frequencies, the tuning function 64 adjusts the output voltage and/or current to maintain a constant output power level (p-constant). The function 64 also senses changes in transducer impedance (see FIG. 8B)—Z-min to Z-max—throughout the frequency sweep. In this approach (see FIG. 8B), the tuning function 64 selects as the frequency of operation the frequency (f-tune) where, during the sweep, the minimum magnitude of transducer impedance (Z-min) is sensed. Typically, this is about the same as the frequency of maximum output current (I), which in turn, is about the same as the frequency of minimum output voltage (V).

In an alternative frequency selection approach, the tuning function 64 can select as the frequency of operation the frequency where, during the sweep, the maximum of real transducer impedance (Z) occurs, where:

$$|Z|=\sqrt{(R^2+X^2)}$$

and where |Z| is the absolute value of the transducer impedance (Z), which derived according to the following expression:

$$Z=R+iX$$

where R is the real part, and X is the imaginary part.

In another alternative frequency selection approach, while sweeping the frequencies, the tuning function 64 can maintain a constant output voltage. In this approach, the tuning function 64 can select as the frequency of operation the frequency where, during the sweep, the maximum output power occurs. Alternatively, the tuning function 64 can select as the frequency of operation the frequency where, during the sweep, the maximum output current occurs.

B. Power Ramping

As before described, the tuning function 64 desirably operates an output power level lower than the output power level of treatment. In this arrangement, once the operating frequency has been selected, the output power level needs to be increased to the predetermined output level to have the desired therapeutic effect.

In the illustrated embodiment (see FIG. 10), the controller 26 includes a ramping function 66. The ramping function 66 (see FIG. 9) causes a gradual ramp up of the output power level from the power level at which the tuning function 64 is conducted (e.g., 5 W) to the power level at which treatment occurs (e.g., 25 W). The gradual ramp up decreases the possibility of unwanted patient reaction to the ultrasound exposure. Further, a gradual ramp up is likely to be more comfortable to the patient than a sudden onset of the full output power.

In a desired embodiment, the ramping function 66 increases power at a rate of about 0.01 W/s to about 10 W/s. A particularly desired ramping rate is between about 0.1 W/s to about 5 W/s. The ramping function 66 desirably causes the ramp up in a linear fashion (as FIG. 9 shows). However, the ramping function can employ non-linear ramping schemes, e.g., logarithmic or according to another mathematical function.

C. Output Power Control

Also depending upon the treatment parameters and outcome desired, the controller 26 can operate a given transducer 40 at a prescribed power level, which can remain fixed or can be varied during the treatment session. The controller 26 can also operate one or more transducers 40 within an array of transducers 40 (or when using multiple applicators 18) at different power levels, which can remain fixed or themselves vary over time.

The parameters affecting power output take into account the output of the signal generator module; the physical dimensions and construction of the applicator; and the physiology of the tissue region to which ultrasonic energy is being applied.

During a given treatment session, the transducer impedance may vary due to a number of reasons, e.g., transducer heating, changes in acoustic coupling between the transducer and patient, and/or changes in the transducer bladder fill volume due to degassing and/or leaks. In the illustrated embodiment (see FIG. 10), the controller 26 includes an output power control function 68. The output power control function 68 holds the output power constant, despite changes in transducer impedance within a predetermined range. If the transducer falls out of the predetermined range, for instance, due to an open or a short circuit, the controller 26 shutdowns the generator ultrasound module 24 and desirably sounds an alarm.

Governed by the output power control function 68, as the transducer impedance increases, the output voltage is increased to hold the power output constant. Should the output voltage reach a preset maximum allowable value, the output power will decrease, provided the transducer impedance remains within its predetermined range. As the transducer impedance subsequently drops, the output power will recover, and the full output power level will be reached again.

Governed by the output power control function 68, as the transducer impedance decreases, the output current is increased to hold the power output constant. Should the output current reach a preset maximum allowable value, the output power will decrease until the impedance increases, again, and will allow full output power.

In addition to the described changes in the output voltage and current to maintain a constant output power level, the output power control function 68 can vary the frequency of operation slightly upward or downward to maintain the full output power level within the allowable current and voltage limits.

D. Pulsed Power Mode

The application of ultrasonic energy in a pulsed power mode can serve to reduce the localized heating effects that can arise due to operation of the transducer 40.

During the pulsed power mode, ultrasonic energy is applied at a desired fundamental frequency or within a desired range of fundamental frequencies at the prescribed power level or range of power levels (as described above, to achieve the desired physiologic effect) in a prescribed duty cycle (DC) (or range of duty cycles) and a prescribed pulse repetition frequency (PRF) (or range of pulse repetition frequencies). Desirably, the pulse repetition frequency (PRF) is between about 20 Hz to about 50 Hz (i.e, between about 20 pulses a second to about 50 pulses a second).

The duty cycle (DC) is equal to the pulse duration (PD) divided by one over the pulse repetition frequency (PRF). The pulse duration (PD) is the amount of time for one pulse. The pulse repetition frequency (PRF) represents the amount of time from the beginning of one pulse to the beginning of the next pulse. For example, given a pulse repetition frequency (PRF) of 30 Hz (30 pulses per second) and a duty cycle of 25% yields a pulse duration (PD) of approximately 8 msec. At these settings, the system outputs an 8 msec pulse followed by a 25 msec off period 30 times per second.

Given a pulse repetition frequency (PRF) selected at 25 Hz and a desired fundamental frequency of 27 kHz delivered in a power range of between about 15 to 30 watts, a duty cycle of about 50% or less meets the desired physiologic objectives in the thoracic cavity, with less incidence of localized conductive heating effects compared to a continuous application of the same fundamental frequency and power levels over a comparable period of time. Given these operating conditions, the duty cycle desirably lays in a range of between about 10% and about 35%.

III. Monitoring Use of the Transducer

To protect patients from the potential adverse consequences occasioned by multiple use, which include disease transmission, or material stress and instability, or decreased or unpredictable performance, the controller 26 desirably includes a use monitoring function 70 (see FIG. 10) that monitors incidence of use of a given transducer 40.

In the illustrated embodiment, the transducer 40 carries a use register 72 (see FIG. 4) The use register 72 is configured to record information before, during, and after a given treatment session. The use register 72 can comprise a solid state micro-chip, ROM, EEROM, EPROM, or non volatile RAM (NVRAM) carried by the transducer 40.

Figure 11:
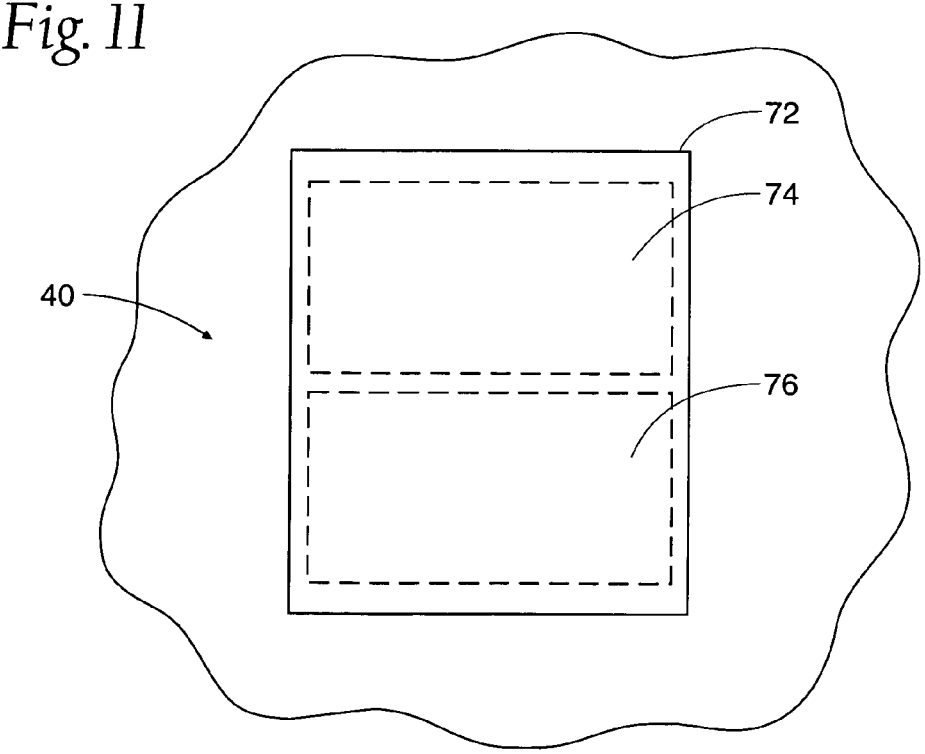
FIG. 11 is a diagrammatic view of a use register chip that forms a part of the use monitoring function shown in FIG. 10.

The use register 72 is initially formatted and programmed by the manufacturer of the system to include memory fields. In the illustrated embodiment (see FIG. 11), the memory fields of the use register are of two general types: Write Many Memory Fields 74 and Write-Once Memory Fields 76. The Write Many Memory Fields 74 record information that can be changed during use of the transducer 40. The Write-Once Memory Fields 76 record information that, once recorded, cannot be altered.

The specific information recorded by the Memory Fields 74 and 76 can vary. The following table exemplifies typical types of information that can be recorded in the Write Many Memory Fields 74.

| Field Name | Description | Location | Size (Byte) |
| --- | --- | --- | --- |
| Treatment Complete | If a transducer has been used for a prescribed maximum treatment time (e.g., 60 minutes), the treatment complete flag is set to 1 otherwise it is zero. | 0 | 1 |
| Prescribed Maximum Treatment Time (Minutes) | This is the allowable usage time of the transducer. This is set by the manufacturer and determines at what point the Treatment Complete flag is set to 1. | 1–2 | 2 |
| Elapsed Usage Time (Minutes) | Initialized to zero. This area is then incremented every minute that the system is transmitting ultrasound energy. This area keeps track of the | 3–4 | 2 |

-continued

| Field Name | Description | Location | Size (Byte) |
| --- | --- | --- | --- |
| | amount of time that the transducer has been used. When this time reaches the Prescribed Maximum Treatment Time, the Treatment Complete flag is set to 1. | | |
| Transducer Frequency | This is an area that could be used to prescribe the operational frequency of the transducer, rather than tuning the transducer to an optimal frequency, as above described. In the latter instance, this area shows the tuned frequency once the transducer has been tuned. | 5–6 | 2 |
| Average Power (Watts) | The system reads and accumulates the delivered power throughout the procedure. Every minute, the average power number is updated in this area from the system, at the same time the Elapsed Usage Time is updated, when the Usage time clock is updated. This means that the average power reading could be off by a maximum of 59 seconds if the treatment is stopped before the Treatment Complete flag is set. This average power can be used as a check to make sure that the system was running at full power during the procedure. | 7–8 | 2 |
| Applicator CRC | Use Register CRC. This desirably uses the same CRC algorithm used to protect the controller ROM. | 9–10 | 2 |
| Copyright Notice | Desirably, the name of the manufacturer is recorded in this area. Other information can be recorded here as well. | 11–23 | 11 |

The on/off cycles of ultrasound transmission could affect the accuracy of the recorded power levels because of the variance of the power levels due to ramping function 66. For this reason it may be advantageous to also record the number of on/off cycles of ultrasound transmission. This will help explain any discrepancies in the average power reading. It might also allow the identification of procedural problems with system use.

Each use register 72 can be assigned a unique serial number that could be used to track transducers in the field. This number can be read by the use monitoring function 70 if desired.

The following table exemplifies typical types of information that can be recorded in the Write-Once Memory Fields 76.

| Field Name | Description | Size (Bytes) |
| --- | --- | --- |
| Start Date Time | Once the system has tuned the transducer and started to transmit ultrasound, the current date and time are written to this area. This area is then locked, which prevents the data from ever-being changed. | |
| Tuned Frequency | The tuned frequency is written to this location when the Start Date and Time is set. This prevents this information from being written over on subsequent tunes (if necessary). | |

Figure 12:
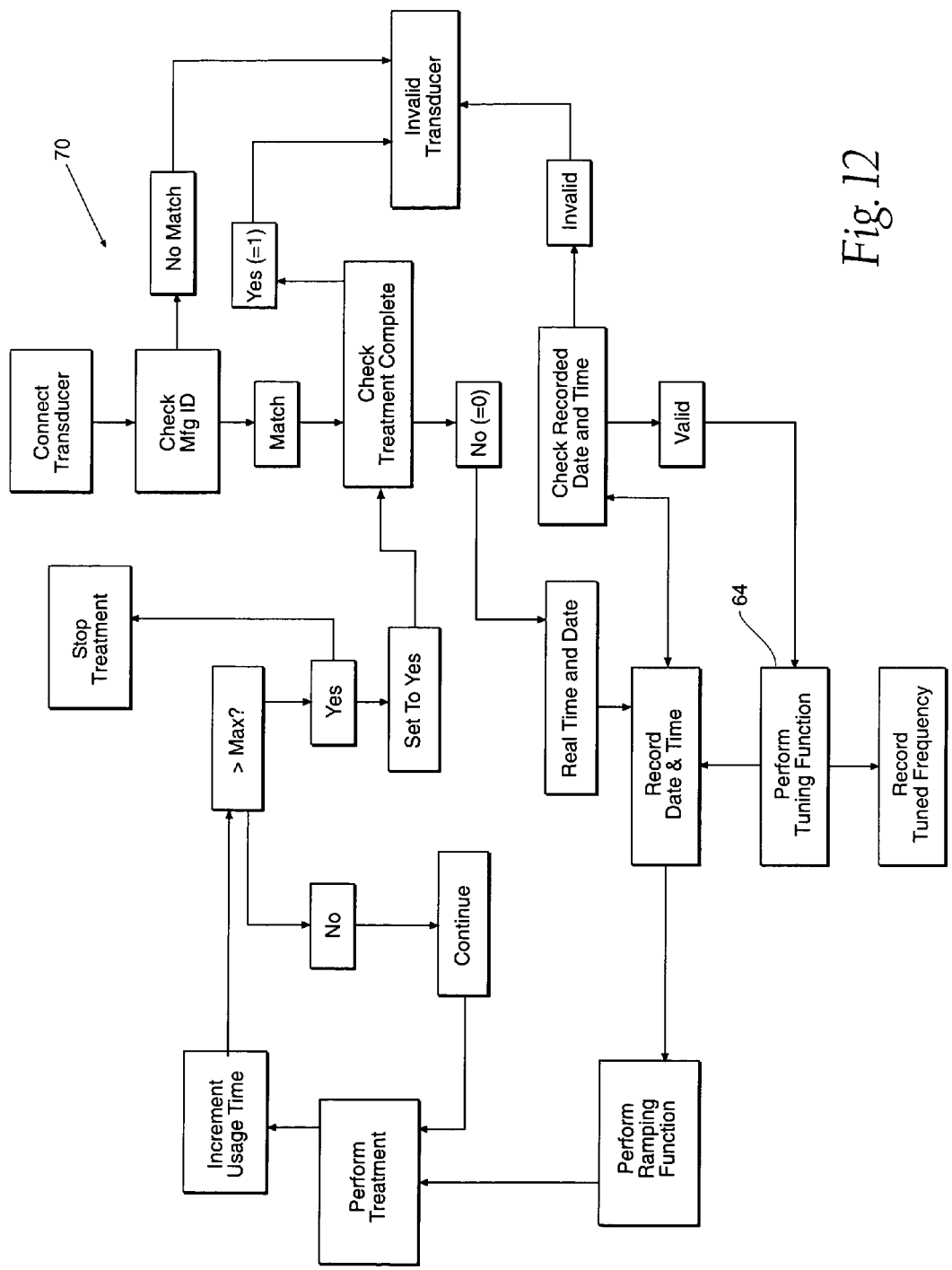
FIG. 12 is a diagrammatic flow chart showing the technical features of the use monitoring function shown in FIG. 10.

As FIG. 12 shows, when a transducer 40 is first coupled to the machine 16, and prior to enabling the conveyance of ultrasound energy to the transducer 40, the use monitoring function 70 prompts the use register 72 to output resident information recorded in the memory fields.

The use monitoring function 70 compares the contents of the Copyright Notice field to a prescribed content. In the illustrated embodiment, the prescribed content includes information contained in the Copyright Notice field of the Write Many Memory Fields 74. The prescribed content therefore includes the name of the manufacturer, or other indicia uniquely associated with the manufacture. If the prescribed content is missing, the use monitoring function 70 does not enable use of the transducer 40, regardless of the contents of any other memory field. The transducer 40 is deemed "invalid." In this way, a manufacturer can assure that only transducers meeting its design and quality control standards are operated in association with the machine 16.

If the contents of the Copyright Notice field match, the use monitoring function 70 compares the digital value residing in the Treatment Complete field of the Write Many Memory Fields 74 to a set value that corresponds to a period of no prior use or a prior use less than the Prescribed Maximum Treatment Time—i.e., in the illustrated embodiment, a zero value. A different value (i.e., a 1 value) in this field indicates a period of prior use equal to or greater than the Prescribed Maximum Treatment Time. In this event, the use monitoring function 70 does not enable use of the transducer 40. The transducer 40 is deemed "invalid."

If a value of zero resides in the Treatment Complete field, the use monitoring function 70 compares the date and time data residing in the Write-Once Start Date and Time field to the current date and time established by a Real Time Clock. If the Start Date and Time is more than a prescribed time before the Real Time (e.g., 4 hours), the controller does not enable use of the transducer 40. The transducer 40 is deemed "invalid."

If the Start Date and Time field is empty, or if it is less than the prescribed time before the Real Time, the use monitoring function 70 deems the transducer 40 to be "valid" (providing the preceding other criteria have been met). The use monitoring function 70 reports a valid transducer to the controller 26, which initiates the tuning function 64. If the Start Date and Time field is empty, once the tuning function 64 is completed, the controller prompts the use monitoring function 70 to records the current date and time in the Start Date and Time Field, as well as the selected operating frequency in the Tuned Frequency field. The controller 26 then proceeds to execute the ramping function 66 and, then, execute the prescribed treatment protocol.

If the Start Date and Time field is not empty (indicating a permitted prior use), once the tuning function 64 is completed, the controller 26 immediately proceeds with the ramping function 66 and, then, execute the treatment protocol.

During use of the transducer 40 to accomplish the treatment protocol, the use monitoring function 70 periodically updates the Elapsed Usage Time field and Average Power field (along with other Many Write Memory Fields). Once the Treatment Complete flag is set to a 1 value (indicating use of the transducer beyond the Prescribed Maximum Treatment Time), the use monitoring function 70 interrupts the supply of ultrasound energy to the transducer. The transducer 40 is deemed "invalid" for subsequent use. The use monitoring function 70 can also generate an output that results in a visual or audible alarm, informing the operator that the transducer 40 cannot be used.

The information recorded in the use register 72 can also be outputted to monitor use and performance of a given transducer 40. Other sensors can be used, e.g., a temperature sensor 78 carried on the front mass piece 32 (see FIG. 4), in association with the use register.

As described, the use register 72 allows specific pieces of information to be recorded before, during and after a treatment is complete. Information contained in the use register 72 is checked before allowing use of a given transducer 40. The use register 72 ensures that only a transducer 40 having the desired design and performance criteria imparted by the manufacturer can be used. In addition, the use register 72 can be used to "lock out" a transducer 40 and prevent it from being used in the future. The only way the transducer 40 could be reused is to replace the use register 72 itself. However, copying the architecture of the use register 72 (including the contents of the Copyright Message field required for validation) itself constitutes a violation of the manufacturer's copyright in a direct and inescapable way.

Various features of the invention are set forth in the following claims.

We claim:

1. A system comprising
an ultrasound transducers,
an ultrasound generator coupled to the ultrasound transducer for operation,
a use register sized and configured to be carried by the ultrasound transducer, the use register comprising memory fields including a first memory field that registers, according to preprogrammed rules, a prescribed copyright notice a second memory field that registers, according to the preprogrammed rules, a prescribed maximum usage time for the ultrasound transducer, and a third memory field that registers a frequency tuned for the ultrasound transducer according to the preprogrammed rules for the maximum usage time, the third memory field comprising a write-once memory field that once written to, according to the preprogrammed rules, cannot be written over, and
a use monitoring controller sized and configured to be carried by the ultrasound generator and to be coupled to the use register to control delivery of ultrasound energy through the ultrasound transducer according to the preprogrammed rules comprising a first preprogrammed rule that compares the prescribed copyright notice in the first memory field to a prescribed content and disables use of the ultrasound transducer if the prescribed content is not present in the first memory field; a second preprogrammed rule that, only if the prescribed content is present in the first memory field and only if the third memory field has not been previously written to, selects a tuned frequency for the ultrasound transducer and writes the tuned frequency to the third memory field; a third preprogrammed rule that delivers ultrasound energy to the ultrasound transducer only at the tuned frequency written to the third memory field; and a fourth preprogrammed rule that disables operation of the ultrasound transducer at the end of the prescribed maximum usage time registered in the second memory field.

2. A system according to claim 1
wherein the use register includes an additional memory field for incrementally registering an elapsed time of operation following an instance of first operation, and
wherein the fourth preprogrammed rule includes an elapsed time validation function that compares the elapsed time of operation registered in the additional memory field with the prescribed maximum usage time registered in the second memory field.

3. A method comprising
providing an ultrasound transducer
providing an ultrasound generator,
coupling a use register to the ultrasound transducer comprising that includes a first memory field that registers, according to preprogrammed rules, a prescribed copyright notice, a second memory field that registers, according to the preprogrammed rules, a prescribed maximum usage time for the ultrasound transducer, and a third memory field that registers a frequency tuned for the ultrasound transducer according to the preprogrammed rules for the maximum usage time, the third memory field comprising a write-once memory field that once written to, according to the preprogrammed rules, cannot be written over,
coupling a use monitoring controller to the ultrasound generator to control delivery of ultrasound energy through the ultrasound transducer according to the preprogrammed rules comprising a first preprogrammed rule that compares the prescribed copyright notice in the first memory field to a prescribed content and disables use of the ultrasound transducer if the prescribed content is not present in the first memory field; a second preprogrammed rule that, only if the prescribed content is present in the first memory field and only if the third memory field has not been previously written to, selects a tuned frequency for the ultrasound transducer and writes the tuned frequency to the third memory field; a third preprogrammed rule that delivers ultrasound energy to the ultrasound transducer only at the tuned frequency written to the third memory field; and a fourth preprogrammed rule that disables operation of the ultrasound transducer at the end of the prescribed maximum usage time registered in the second memory field,
coupling the use register of the ultrasound transducer to the use monitoring controller of the ultrasound generator,
executing the first preprogrammed rule and disabling operation of the ultrasound transducer if the prescribed content is not present the first memory field,
executing the second preprogrammed rule only if the prescribed content is present in the first memory field and only if the third memory field has not been previously written to, and
executing the third preprogrammed rule to deliver ultrasound energy to the ultrasound transducer only at the tuned frequency written to the third memory field; and
executing the fourth preprogrammed rule to disable operation of the ultrasound transducer at the end of the prescribed maximum usage time registered in the second memory field.

4. A method according to claim 3
wherein the ultrasound energy delivered to the ultrasound transducer is transcutaneously applied to a targeted tissue region.

* * * * *